(12) United States Patent
Solazzo et al.

(10) Patent No.: US 8,471,715 B2
(45) Date of Patent: Jun. 25, 2013

(54) DISPOSABLE DIAPER WITH WIRELESS ALARM SYSTEM

(76) Inventors: Anthony Solazzo, Watchung, NJ (US); Herbert Heflich, Martinsville, NJ (US)

( * ) Notice: Subject to any disclaimer, the term of this patent is extended or adjusted under 35 U.S.C. 154(b) by 301 days.

(21) Appl. No.: 12/931,808

(22) Filed: Feb. 11, 2011

(65) Prior Publication Data

US 2012/0206265 A1    Aug. 16, 2012

(51) Int. Cl.
*G08B 23/00*    (2006.01)
*G08B 1/08*    (2006.01)
*A61F 13/15*    (2006.01)
*H01H 29/00*    (2006.01)

(52) U.S. Cl.
USPC ........... 340/573.5; 340/573.6; 340/539.1; 340/604; 200/61.04; 200/DIG. 41; 604/361

(58) Field of Classification Search
USPC ....................................................... 340/573.5
See application file for complete search history.

(56) References Cited

U.S. PATENT DOCUMENTS

| | | |
|---|---|---|
| 3,759,246 A | 9/1973 | Flack et al. |
| 5,392,032 A | 2/1995 | Kline et al. |
| 5,463,377 A | 10/1995 | Kronberg |
| 5,570,082 A | 10/1996 | Mahgerefteh et al. |
| 6,097,297 A * | 8/2000 | Fard .............................. 340/604 |
| 6,384,728 B1 | 5/2002 | Kanor et al. |
| 6,774,800 B2 | 8/2004 | Friedman et al. |
| 7,431,716 B2 | 10/2008 | Tracy |
| 2003/0011479 A1* | 1/2003 | Bluteau ...................... 340/573.5 |
| 2008/0129519 A1 | 6/2008 | Gabriel |
| 2008/0132859 A1* | 6/2008 | Pires ............................ 604/361 |

* cited by examiner

*Primary Examiner* — Donnie Crosland
(74) *Attorney, Agent, or Firm* — Francis C. Hand; Carella, Byrne et al

(57) ABSTRACT

A disposable diaper with wireless alarm system includes a) a disposable diaper structure; b) a disposable diaper telltale conductive strip; c) an attachable, removable, reusable battery-powered sensor-transmitter device; and d) a wireless receiver with an alarm signal. Multiple diapers with different frequencies and optional disconnect sensors may be included and controlled by local or remote computer.

20 Claims, 14 Drawing Sheets

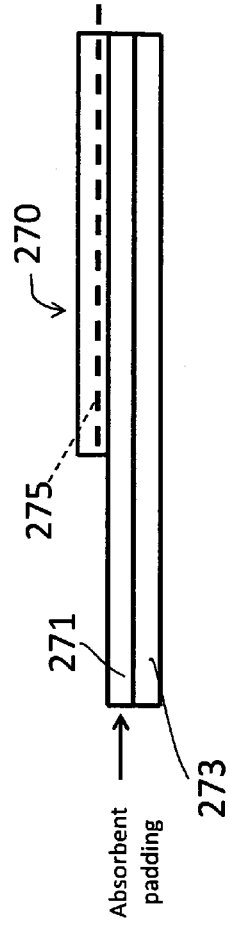
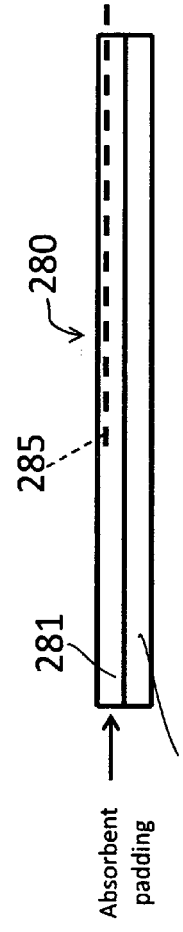
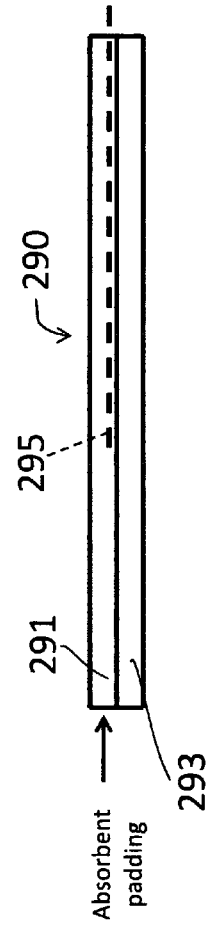
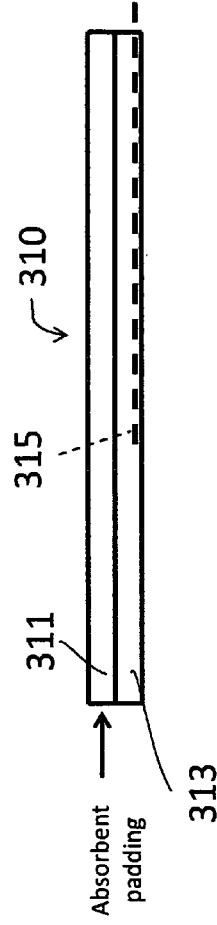

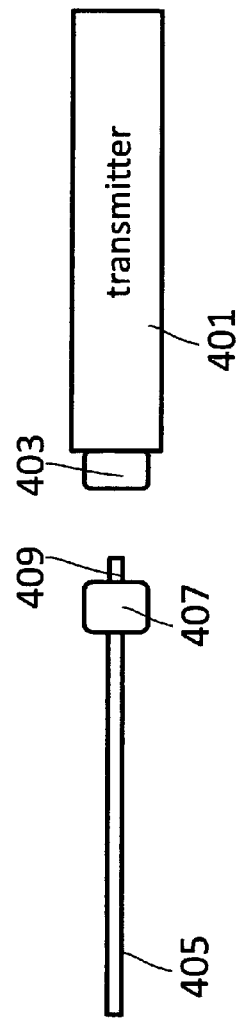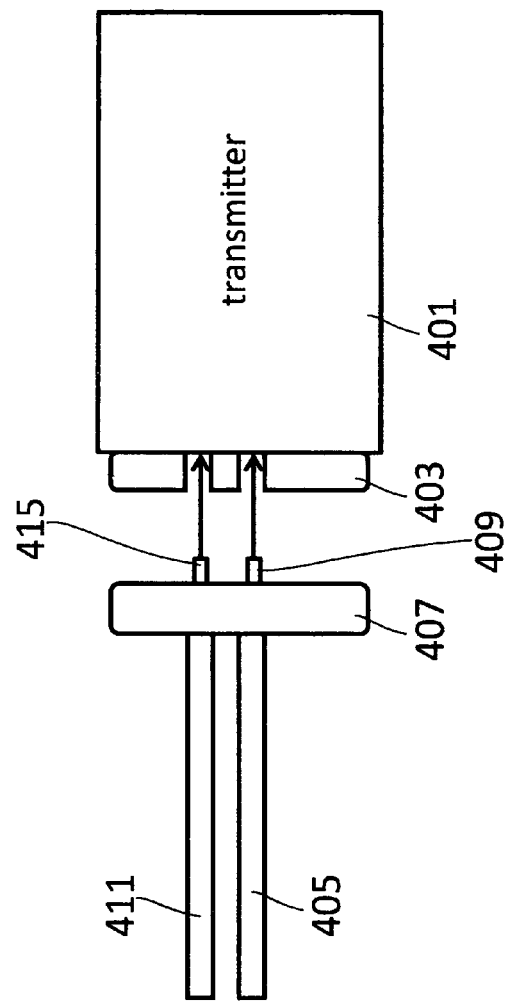

Figure 17A
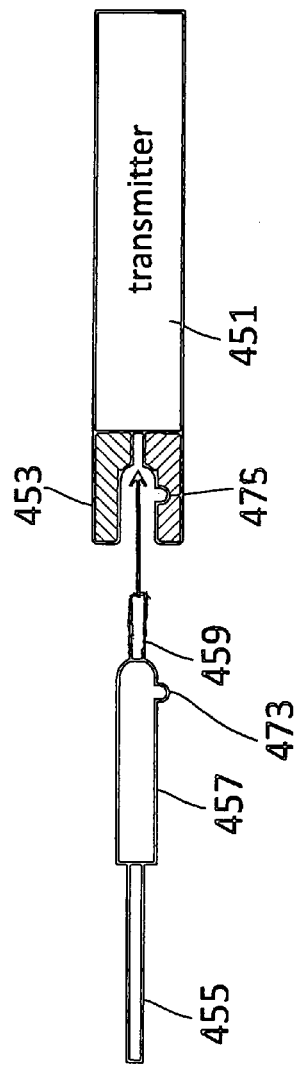
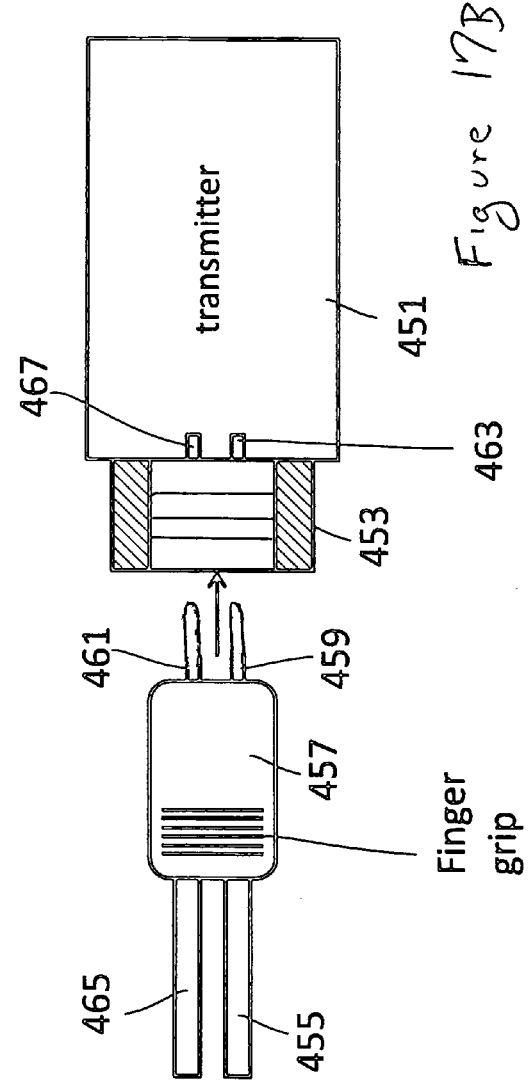
Figure 17B

DISPOSABLE DIAPER WITH WIRELESS ALARM SYSTEM

BACKGROUND OF INVENTION a. Field of Invention

The invention relates generally to the problem of diapers not being changed in a timely fashion when the y have been soiled. This need relates to baby diapers, incontinence diapers, and seniors' diapers. It is a very serious problem for nursing homes, hospitals and other senior care facilities, as well as for other caretakers. The present invention involves a wireless alarm system to advise any caretaker in the vicinity of a receiver, that a diaper needs to be changed. The present invention devices and systems are particularly advantageous for a number of reasons. The inserted conductive strips are disposable and need not be removed from the disposable diapers; the transmitter is detachable and may be reused many times over; the alarm signal is wireless and the receiver need not be in the same room or area as the diaper wearer.

The present invention systems may further include dual monitoring: fist, to assure that the transmitter is connected to the conductive strip; and second, to signal an alarm when a diaper is adequately wet to close the conductive strip circuit and transmit the alarm frequency to the receiver. In some embodiments, the transmitters all have different frequencies and a wireless receiver and controller will handle multiple patients (diaper users) simultaneously and identify the particular patient that is in need of a diaper change. In some embodiments, the receiver/controller is a computer with sufficient software to maintain a computerized history (tracking) so that care records for each patient may be preserved and reviewed.

b. Description of Related Art

The following patents are representative of the field pertaining to the present invention:

U.S. Pat. No. 7,431,716 to Tracy describes a disposable diaper having a diaper body including an inner lining comprising a liquid-absorbent material and a removable core shaped to engage a portion of the inner lining. The removable core is temporarily secured to the diaper body and is removable therefrom.

U.S. Pat. No. 6,774,800 B2 to Friedman et al. describes a patient fluid discharge monitoring method and apparatus includes at least one article configured to be worn by a patient, the article having absorbent material and a RF tag received adjacent the absorbent material. The RF tag is excited with an excitation signal and the response of the RF tag to the excitation signal is detected. The detected response of the RF tag is compared to a predetermined response. The RF tag has a first detected response when the absorbent material has no fluid the rein and a second detected response when the absorbent material has fluid the rein.

U.S. Pat. No. 6,384,728 B1 to Kanor et al. describes a personal care monitoring system having at least one condition detecting sensor and a corresponding condition indicator. The condition-detecting sensor may indicate detection of wetness, such as caused by enuresis. Alternatively, or additionally, the condition-detecting sensor may indicate that the physical position of the wearer of the device has not been adjusted for over a predetermined amount of time after which the likelihood of the development of bedsores increases. The indicator may be any desired type of indicator, preferably alerting one of the senses that the monitored condition has been detected. For instance, the indicator may be a light, an audible alarm, or a vibrating device. A processing means preferably is provided to control operation of the various components of the monitoring system. Moreover, the processing means may be programmed to store information pertaining to the operation of the components of the monitoring system. For example, the time at which a condition has been detected as well as the time at which a caregiver has attended to the condition may be recorded. Such information may be retrieved to determine the frequency of care given to the wearer of the monitoring system as well as the amount of time elapsed between occurrence of the monitored condition and attendance to such condition by the caregiver.

U.S. Pat. No. 5,570,082 to Mahgerefteh, et al. describes a system for detecting wetness in diapers for the propose of calling the attention of a caretaker. The system is based on the nonlinear interaction of an implanted device inside the diaper with a low distortion background electromagnetic field. The background field is generated by a transmitter external to the diaper. The device is a combination of an antenna, a nonlinear element and two electrodes. Upon a wet condition, the resistance between the two electrodes decreases, resulting in an increase in coupling between the antenna and the nonlinear element. The ensuing nonlinear interaction between the antenna and the background field gives rise to harmonics of the field that are detected by a receiver. The receiver that is also external to the diaper triggers a suitable alarm.

U.S. Pat. No. 5,463,377 to Kronberg describes an apparatus for detecting the presence of a liquid in a region, including an electrically passive sensor adapted for contacting the liquid, and an electrically active detector. The sensor is a circuit with a pair of spaced-apart terminals connected to a switch that closes in the presence of the liquid. The detector carries an alternating current with a resonant frequency. When the sensor is placed in a region and liquid is present in the region, the circuit of the sensor is closed. By bringing the detector close to the sensor, an alternating current is induced in the sensor that will, in turn, alter the resonant frequency of the detector. The change in the resonant frequency is signaled by a transducer. The switch can operate by a change in conductivity of a material between the terminals of the sensor or by expansion of a liquid absorber that pushes the two terminals together, or by a change in the conductivity of the space between the terminals as a result of the presence of the liquid. The detector generates an audible or visible signal, or both, in response to the change in current.

U.S. Pat. No. 5,392,032 to Kline et al. describes a device for signaling a wet condition in a diaper. The device includes a sensing means for sensing wet conditions in the diaper and signal means connected to the sensing means for producing a signal substantially concurrently with sensing the wet conditions in the diaper. The sensing means are insulated from the wearer when the diaper is dry and are activated by the diaper once the diaper becomes wet.

U.S. Pat. No. 3,759,246 to Flack et al. describes urinary incontinence can be evaluated both in respect of frequency and quantity by use of a detector device in the form of a flexible sheet of absorbent material having elongate electrodes supported in it in an interleaved, uniformly spaced array. This device is worn as a diaper and any incontinence will vary and be detectable and measurable by the electrical conductivity of the sheet material between the electrodes. Any undesirable variations in this technique due to compression of the sheet in use can be offset by supporting the electrodes in a waved manner along their lengths and through the sheet thickness, and by quilting the sheet. Other variations due to differing urine salts content can be taken into account by pre-loading the sheet with a salt to give a datum or bias salt level above which such variations are less significant.

United States Patent Application No. US 2008/0129519 A1 to Gabriel describes a multi-sensor baby care monitoring system includes a wetness sensor configured to generate a first signal relating to an occurrence of a wetness event relative to a wetness containment device, such as a diaper. The monitoring system further includes a human life sensor configured to generate a second signal relating to a presence or absence of a human relative to the wetness containment device. If desired, a system controller may be used for receiving the first and second signals and generating data associated with the wetness event and the presence or absence of said human.

Notwithstanding the prior art, the present invention is neither taught nor rendered obvious thereby.

SUMMARY OF INVENTION

The present invention is a disposable diaper with wireless alarm system. It includes a) a disposable diaper structure; b) a disposable diaper telltale conductive strip; c) an attachable, removable, reusable battery-powered sensor-transmitter device; and d) a wireless receiver with an alarm signal. The disposable diaper structure has at least an inside layer, being a screen layer, a middle layer, being an absorbent layer, and an outer layer, being a barrier layer, and further has at least one fastening mechanism for affixing the disposable diaper structure to a person. The disposable conductive strip is located within the disposable diaper structure, and has two conductive bands and a non-conductive band between the two conductive bands, the two conductive bands are spaced sufficiently to have an open circuit when dry and to have a closed circuit when the strip is wet with urine. The attachable, removable, reusable battery-powered sensor-transmitter device attached to the disposable diaper structure and electrically connected to the two conductive bands of the disposable conductive strip, the sensor-transmitter device having a predetermined frequency for transmittal to a wireless receiver.

The wireless receiver has an alarm signal and is remotely located from the sensor-transmitter device, and set to receive a transmission therefrom. This receiver could be a portable receiver or a stationary one and could be located at a nurse's station or other caretaker's station, in a parent's bedroom or kitchen or other living area. The system functions are follows:

When the disposable contact strip is dry, the sensor-transmitter device does not transmit an alarm signal to the wireless receiver, and when the disposable contact strip is wet with urine to close the circuit, the sensor-transmitter device sends an alarm signal to the wireless receiver, triggering activation of the alarm signal to advise a caretaker that the disposable diaper structure is wet.

In some present invention preferred embodiments, the disposable conductive strip is permanently positioned within the disposable diaper structure. In some other preferred embodiments, the disposable conductive strip is located between the inside layer and the middle layer of the disposable diaper structure. In others, the disposable conductive strip is located within the middle layer of the disposable diaper structure. In yet others, the disposable conductive strip is located between the middle layer and the outer layer of the disposable diaper structure.

In some embodiments of the present invention, the disposable conductive strip is electrically connected to the sensor-transmitter device by a connector mechanism selected from the group consisting of a plug, a hook and loop mechanism, a slide-in receiver for the strip and external contacts.

In different present invention system arrangement, the disposable diaper with wireless alarm system has two alarms, one for on/off connection recognition and one for wet diaper alerts. It includes a) a disposable diaper structure; b) a disposable diaper telltale conductive strip; c) an attachable, removable, reusable battery-powered sensor-transmitter device; and d) a wireless receiver with an alarm signal, as above, but with additional features. The disposable diaper structure has at least an inside layer, being a screen layer, a middle layer, being an absorbent layer, and an outer layer, being a barrier layer, and further has at least one fastening mechanism for affixing the disposable diaper structure to a person. The present invention system disposable conductive strip is located within the disposable diaper structure, and has two conductive bands and a non-conductive band between the two conductive bands, the two conductive bands being spaced sufficiently to have an open circuit when dry and to have a closed circuit when the strip is wet with urine. The non-conductive band is a spacing area and may be an actual structure or just a band of area from a support structure of any type described above or below. There is also an attachable, removable, reusable battery-powered sensor-transmitter device attached to the disposable diaper structure and electrically connected to the two conductive bands of the disposable conductive strip. In these embodiments, the sensor-transmitter device has a first predetermined frequency for transmittal to a wireless receiver to indicate that the disposable conductive strip is electrically connected to the sensor-transmitter device, and it has a second predetermined frequency for transmittal to the wireless receiver when the disposable conductive strip circuit is closed. The wireless receiver is remotely located from the sensor-transmitter device, and is set to receive transmissions therefrom. It has a first receiver corresponding to the first predetermined frequency and has a first predetermined frequency connect signal, to show that the disposable conductive strip is electrically connected to the sensor-transmitter device. It also has a second receiver corresponding to the second predetermined frequency and has a second predetermined frequency wet alarm signal, for activation of a wet diaper structure alarm signal. When the device has the conductive strip electrically connected to the sensor-transmitter, the first frequency signal is not sent or shows connection; when there is a disconnected conductive strip, the first frequency signal sets off a disconnect alarm. Likewise, when the disposable contact strip is dry, the sensor-transmitter device does not transmit a wet alarm signal to the wireless receiver, and when the disposable contact strip is wet with urine to close the circuit, the sensor-transmitter device sends a wet alarm signal to the wireless receiver, triggering activation of that alarm signal to advise a caretaker that the disposable diaper structure is wet. In this double alarm system, in some embodiments, the disposable conductive strip is permanently positioned within the disposable diaper structure. In some other preferred embodiments, the disposable conductive strip is located between the inside layer and the middle layer of the disposable diaper structure. In others, the disposable conductive strip is located within the middle layer of the disposable diaper structure. In yet others, the disposable conductive strip is located between the middle layer and the outer layer of the disposable diaper structure. Also, in some embodiments, the disposable conductive strip is located between the inside layer and the middle layer of the disposable diaper structure. Further, in some embodiments the disposable conductive strip is located within the middle layer of the disposable diaper structure. In some embodiments, the disposable conductive strip is located between the middle layer and the outer layer of the disposable diaper structure. In some embodiments, the disposable conductive strip is electrically connected to the sensor-transmitter device by a connector mechanism selected from the group consisting of a plug, a hook and loop mechanism, a slide-in receiver for the strip and external contacts.

In yet a different format of the present invention, the system is set up for simultaneous multiple diaper users. Thus, here, the present invention disposable diaper wireless alarm system for a plurality of diapers being worn by a plurality of different users, includes a plurality of disposable diapers, a receiver and a controller processor (e.g., a computer, PDA or the like). The plurality of disposable diapers is to be worn or is worn by one of a plurality of different users. Each of the disposable diapers include: (a) a disposable diaper structure having at least an inside layer, being a screen layer, a middle layer, being an absorbent layer, and an outer layer, being a barrier layer, and further having at least one fastening mechanism for affixing the disposable diaper structure to a person; (b) a disposable conductive strip located within the disposable diaper structure, and having two conductive bands and a non-conductive band between the two conductive bands, the two conductive bands being spaced sufficiently to have an open circuit when dry and to have a closed circuit when the strip is wet with urine; (c) an attachable, removable, reusable-battery-powered sensor-transmitter device attached to the disposable diaper structure and electrically connected to the two conductive bands of the disposable conductive strip, the sensor-transmitter device having a predetermined frequency for transmittal to a wireless receiver, and wherein each attachable, removable, reusable battery-powered sensor-transmitter device of the plurality of disposable diapers having different frequencies from all other attachable, removable, reusable battery-powered sensor-transmitter devices so as to identify each user by signals corresponding to the frequencies. The wireless receiver, being remotely located from the sensor-transmitter devices, is set to receive transmissions therefrom, and having plurality of receivers corresponding to the different predetermined frequencies of the sensor-transmitter devices for activation of a wet diaper structure alarm signals. The controller processor connected to the wireless receiver having software to recognize, distinguish and identify different frequency signals and correlate the m to specific transmitters by at least one parameter selected from the group consisting of a unique character identifier, a patient identifier, a transmitter identifier and a location identifier. Thus when the disposable contact strip is dry, the sensor-transmitter device does not transmit an alarm signal to the wireless receiver, and when the disposable contact strip is wet with urine to close the circuit, the sensor-transmitter device sends an alarm signal to the wireless receiver, triggering activation of the alarm signal to advise a caretaker that the disposable diaper structure is wet. In some preferred embodiments of the present invention, the disposable conductive strip is permanently positioned within the disposable diaper structure. In some preferred embodiments of the present invention, the disposable conductive strip is located between the inside layer and the middle layer of the disposable diaper structure. In some preferred embodiments of the present invention, the disposable conductive strip is located within the middle layer of the disposable diaper structure. In some preferred embodiments of the present invention, the disposable conductive strip is located between the middle layer and the outer layer of the disposable diaper structure. In some preferred embodiments of the present invention, the disposable conductive strip is electrically connected to the sensor-transmitter device by a connector mechanism selected from the group consisting of a plug, a hook and loop mechanism, a slide-in receiver for the strip and external contacts. In some preferred embodiments of the present invention, each of the sensor-transmitter devices has a first predetermined frequency for transmittal to the wireless receiver to indicate that the disposable conductive strip is electrically connected to the sensor-transmitter device, and has a second predetermined frequency for transmittal to the wireless receiver when the disposable conductive strip circuit is closed, and wherein each attachable, removable, reusable battery-powered sensor-transmitter device frequency of the plurality of disposable diapers are different frequencies from all other attachable, removable, reusable battery-powered sensor-transmitter device frequencies so as to identify each user by signals corresponding to the frequencies. In some preferred embodiments of the present invention, the system controller processor further includes software, storage and display means to create individual histories of individual diaper structure conductive strip connections, wet alarms and restoration to new diapers, the histories being arranged by at least one parameter selected from the group consisting of a unique character identifier, a patient identifier, a transmitter identifier and a location identifier.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings:

FIGS. 9, 10, 11 and 12 show side partial views of present invention diapers with the conductive strips being positioned above the absorbent padding, within the absorbent padding, between the absorbent padding and the protective outer layer and within the protective outer layer, respectively;

FIGS. 16A and 16B show side and top views of a present invention transmitter connection using plug connectors; and, FIGS. 17A and 17B show side and top views of a present invention transmitter connection using snap-in plug connectors.

DETAILED DESCRIPTION OF THE EMBODIMENTS

Figure 1:
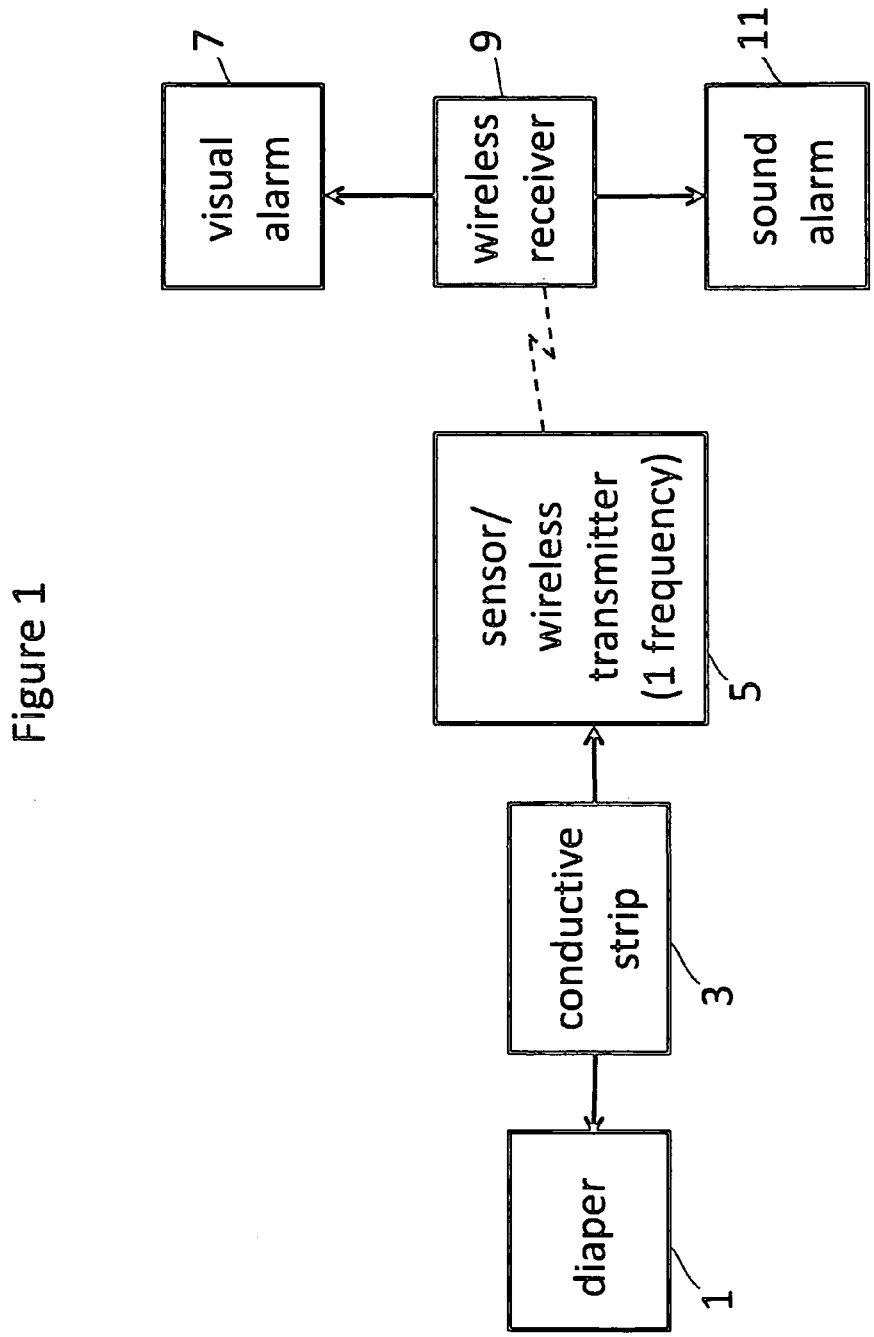
FIG. 1 illustrates a block diagram representing embodiments of the present invention disposable diaper with wireless alarm system involving a single diaper and a single frequency transmission to set off an alarm when the diaper is wet.

Referring now in detail to the drawings wherein like reference numerals designate corresponding parts throughout the several views, various embodiments of the present invention are shown.

FIG. 1 illustrates a block diagram representing embodiments of the present invention disposable diaper 1 with wireless alarm system involving a single diaper and a single frequency transmission to set off an alarm when the diaper is wet. Disposable diaper 1 contains a conductive strip 3 with two separated conductive bands. When conductive liquid (urine) contacts both conductive bands simultaneously, a circuit is completed and sensor/wireless transmitter 5 sends a signal to wireless receiver 9. In response, wireless receiver 9 sets off a "wet diaper" alarm such as a visual alarm 7 or a sound alarm 11. This signals to a caretaker (parent, aide, nurse, or attendant), the need for a diaper change.

The wireless transmitter in any embodiment of the present invention includes standard components well within the skill of the artisan which are not detailed here, as short distance transmitters are well known. In the present invention the power source would be a battery or power cell and could be disposable or rechargeable. Further, in the present invention's systems, the transmitter is physically attached to the diaper so as to be removable and reusable. The present invention system transmitters are removably connected to the conductive strip, because the diaper and conductive strip are integrally formed and disposed together, while the transmitter is, as mentioned, reused.

Figure 2:
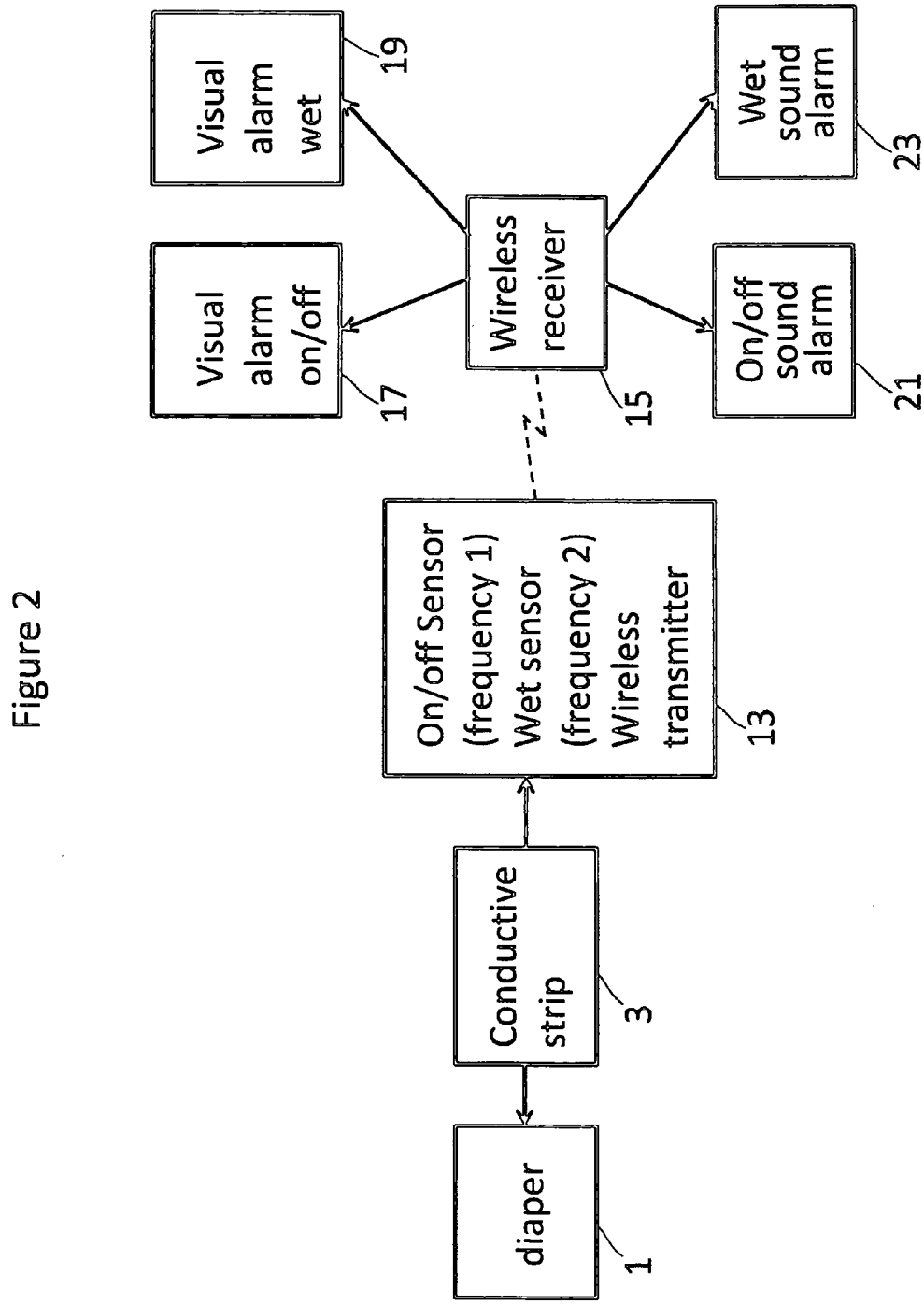
FIG. 2 illustrates a block diagram representing embodiments of the present invention disposable diaper with wireless alarm system involving a single diaper and two different frequency transmissions, one for a disconnect alarm and the other for a wet diaper alarm.

FIG. 2 illustrates a block diagram representing embodiments of the present invention disposable diaper with wireless alarm system involving a single diaper 1 and two different frequency transmissions, one for a disconnect alarm and the other for a wet diaper alarm. Conductive strip 3 operates the same as and is identical to conductive strip 3 described above in conjunction with FIG. 1. However, in this embodiment, sensor/transmitter 13 has two sensors instead of one. Thus, sensor/transmitter 13 has a first sensor that is an on/off sensor that detects whether or not conductive strip 3 is plugged in. If not, then a first frequency signal (frequency 1) is sent to a wireless receiver 15. Wireless receiver 15 has frequency discriminator capabilities and when the first frequency signal is received, wireless receiver 15 will set off an on/off alarm, such as visual alarm 17 or sound alarm 21 or both. Likewise sensor/transmitter 13 has a second sensor that is a wet diaper sensor with a second frequency (frequency 2). When the second frequency signal is received by wireless receiver 15; wireless receiver 15 sets off a wet diaper alarm, such as a visual alarm 19 or sound alarm 23 or both. These alarms will enable caretakers to reconnect disconnected sensors/transmitters, as well as change diapers as needed.

Figure 3:
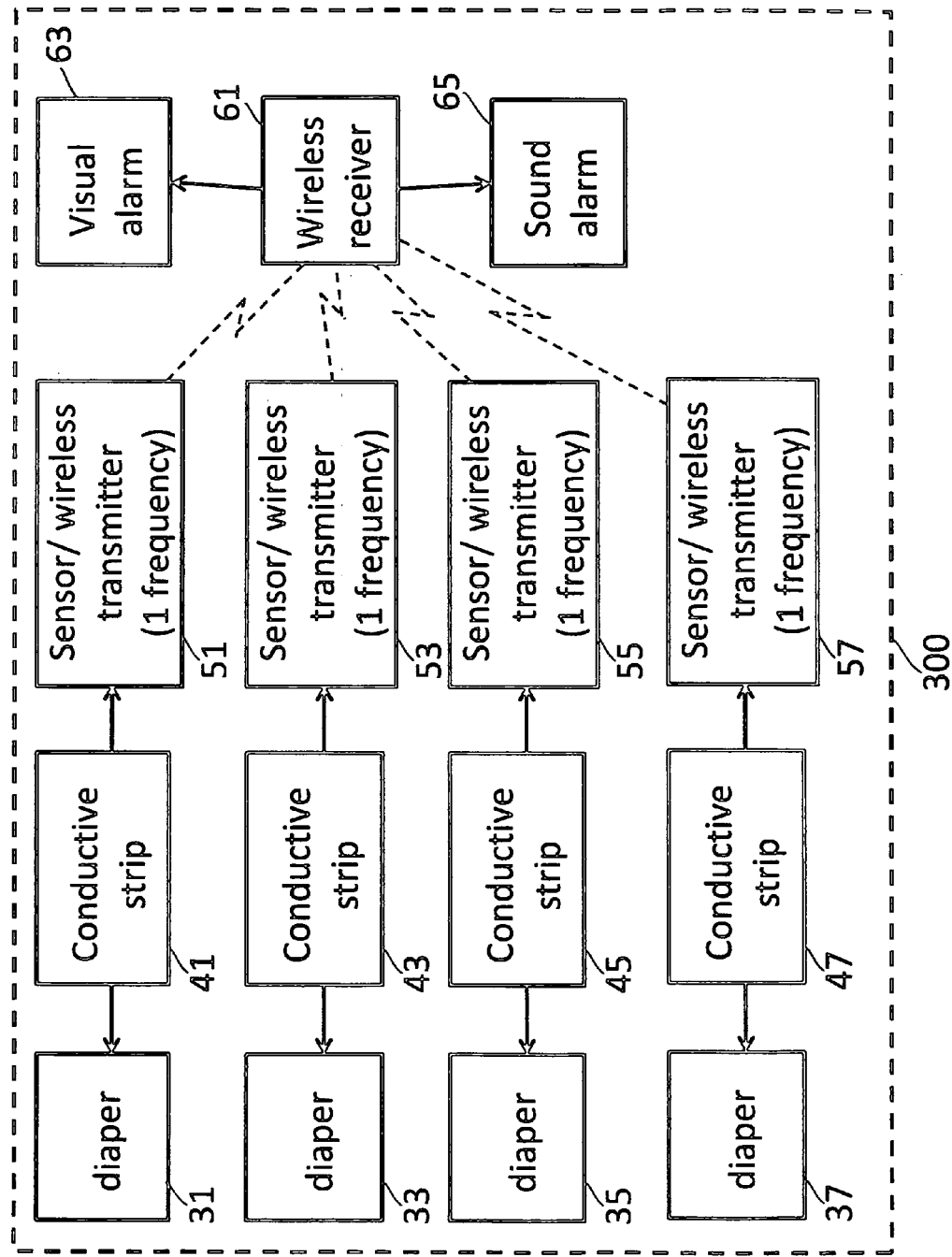
FIG. 3 illustrates a block diagram representing embodiments of the present invention disposable diaper with wireless alarm system involving multiple diapers each with different single frequency transmissions to; set off a wet diaper alarm and to identify the wet diaper.

FIG. 3 illustrates a block diagram representing embodiments of the present invention disposable diaper with wireless alarm system 300 involving multiple diapers each with different single frequency transmissions to set off a wet diaper alarm and to identify the wet diaper. Different users wear diapers 31, 33, 35 and 37 respectively, and each diaper has conductive strips 41, 43, 45 and 47, respectively. They have sensor/transmitters connected to each with wet diaper sensors, and with each transmitter having a single frequency that is different from the other frequencies. Specifically, sensor/wireless transmitters 51, 53, 55, and 57 each have their own different wet diaper transmission frequency. When wireless receiver 61 receives a particular frequency signal, it will set off a defining alarm and will preferably include both visual alarm 63 and sound alarm 65.

Figure 4:
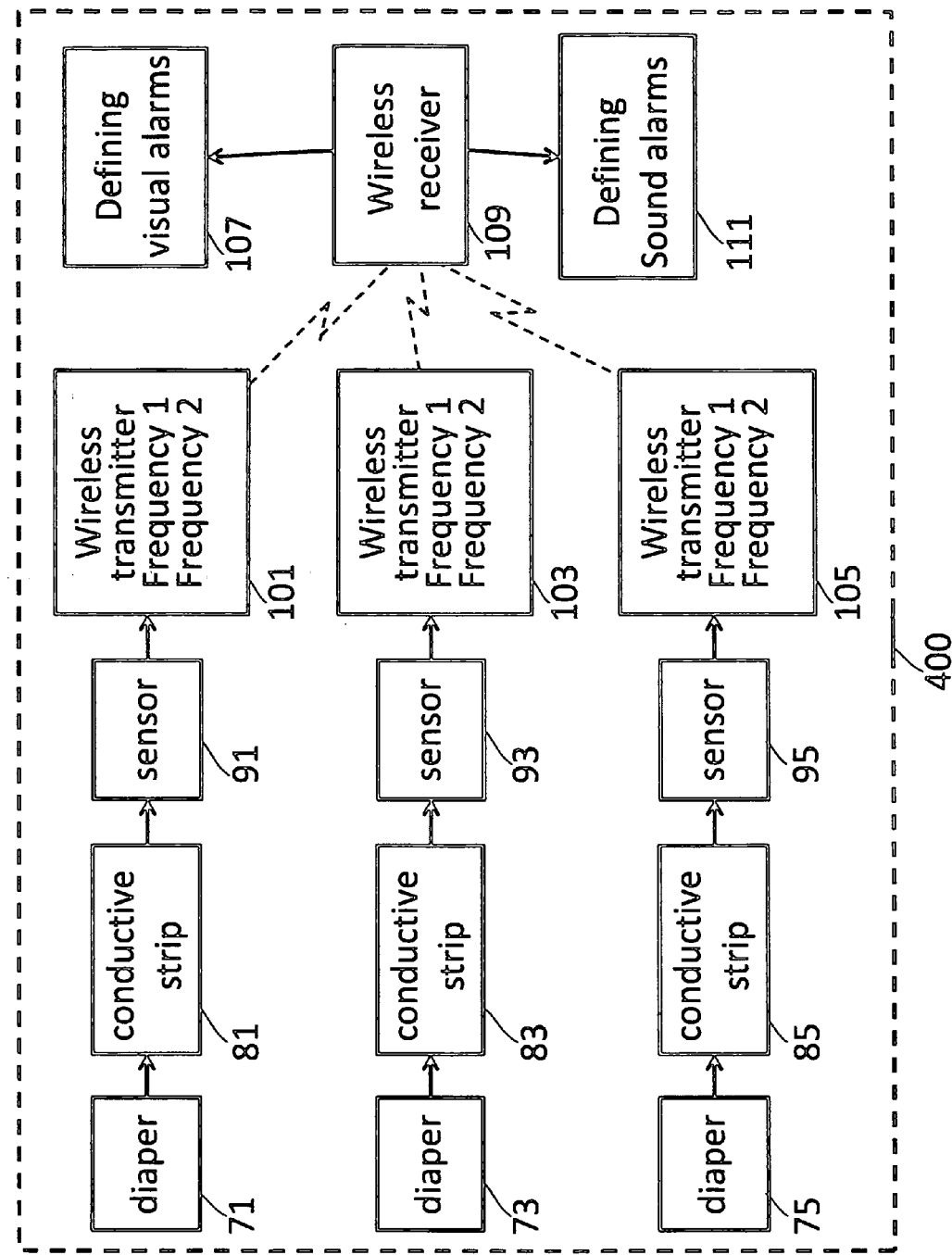
FIG. 4 illustrates a block diagram representing embodiments of the present invention disposable diaper with wireless alarm system involving multiple diapers each with different double frequency transmissions to set off a wet diaper alarm and to identify the wet diaper and to separately set off a disconnect alarm and to identify the disconnected diaper.

FIG. 4 illustrates a block diagram representing embodiments of the present invention disposable diaper with wireless alarm system involving multiple diapers each with different double frequency transmissions to set off a wet diaper alarm and to identify the wet diaper and to separately set off a disconnect alarm and to identify the disconnected diaper. Diapers 71, 73 and 75 are worn by different users and each have conductive strips 81, 83 and 85, respectively. They have sensor/transmitters connected to each with wet diaper sensors and on/off sensors. Each transmitter has two different frequencies that are different from all of the other frequencies in the system. Specifically, sensors 91, 93 and 95 and wireless transmitters 101, 103 and 105 each have their own different wet diaper transmission frequency and their own different on/off transmission frequency. They cooperate to send timely wet diaper or disconnect transmissions to wireless receiver 109. When wireless receiver 109 receives a particular frequency signal, it will set off an identifying alarm and will preferably include both visual alarm 107 and sound alarm 111.

Figure 5:
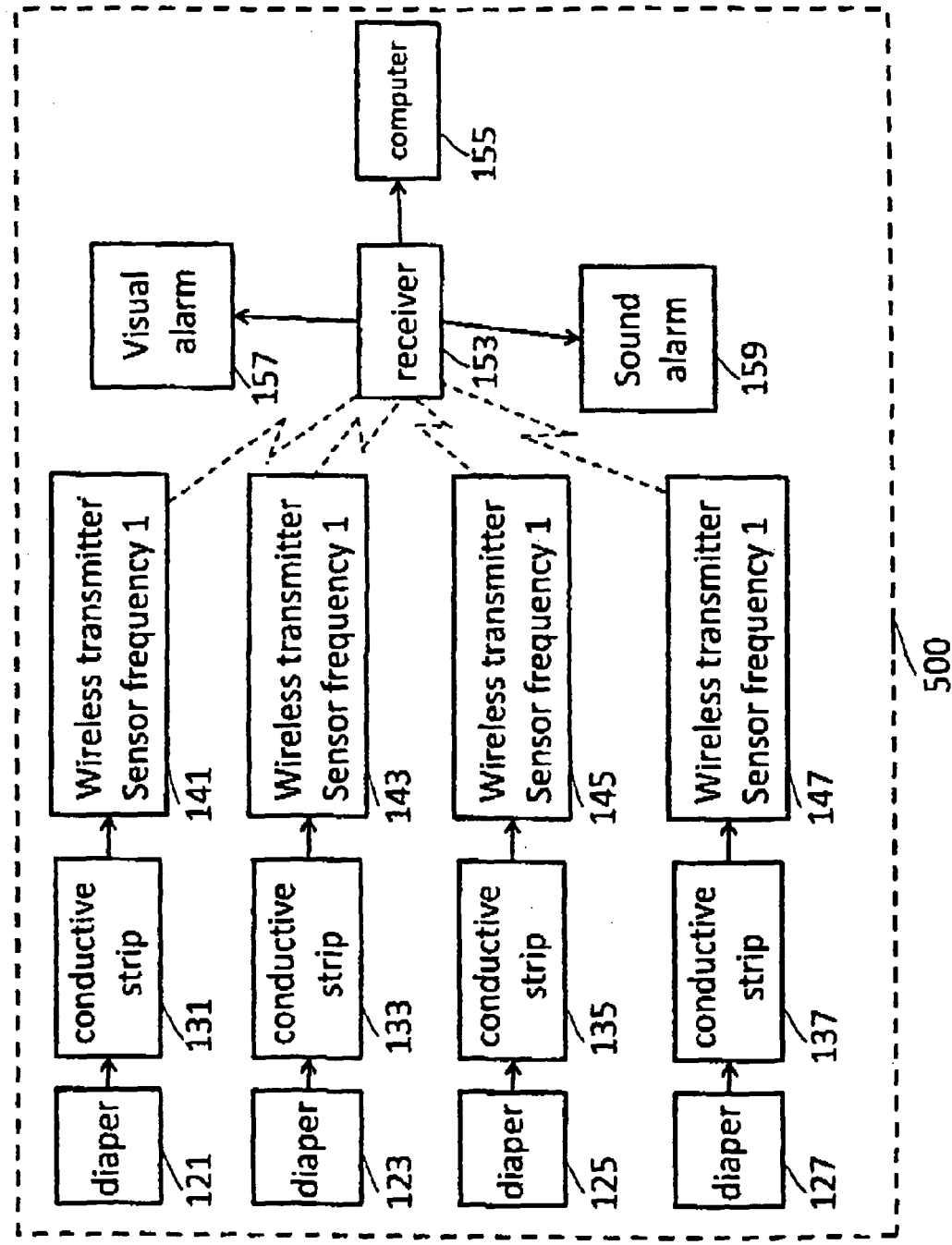
FIG. 5 illustrates a block diagram representing embodiments of the present invention disposable diaper with wireless alarm system involving multiple diapers each with different single frequency transmissions to set off a wet diaper alarm and to identify the wet diaper and further includes a computer controlled system.

FIG. 5 illustrates a block diagram representing embodiments of the present invention disposable diaper with wireless alarm system 500 involving multiple diapers each with different single frequency transmissions to set off a wet diaper alarm and to identify the wet diaper and further includes a computer controlled system. Diapers 121, 123, 125 and 127 are worn by different users and each have conductive strips 131, 133, 135 and 137, respectively. They have sensor/transmitters connected to each with wet diaper sensors, and with each transmitter having a single frequency that is different from the other frequencies. Specifically, sensor/wireless transmitters 141, 143, 145, and 147 each have their own different wet diaper transmission frequency. When wireless receiver 153 receives a particular frequency signal, it will set off a defining alarm that may preferably include both visual alarm 157 and sound alarm 159. Additionally, a process controller, such as computer 155, is connected to the receiver 153 and keeps records of all alarms, e.g., by date, time, wearer, caretaker and alarm type. Computer 155 may also include signal discrimination and control the receiver 153, as well as alarms 157 and 159. Computer 155 may be physically connected to the other components mentioned, or wirelessly connected. It may be physically within the proximity of receiver 153, or remotely located, e.g., so that a supervisor or overseer may monitor operations.

Figure 6:
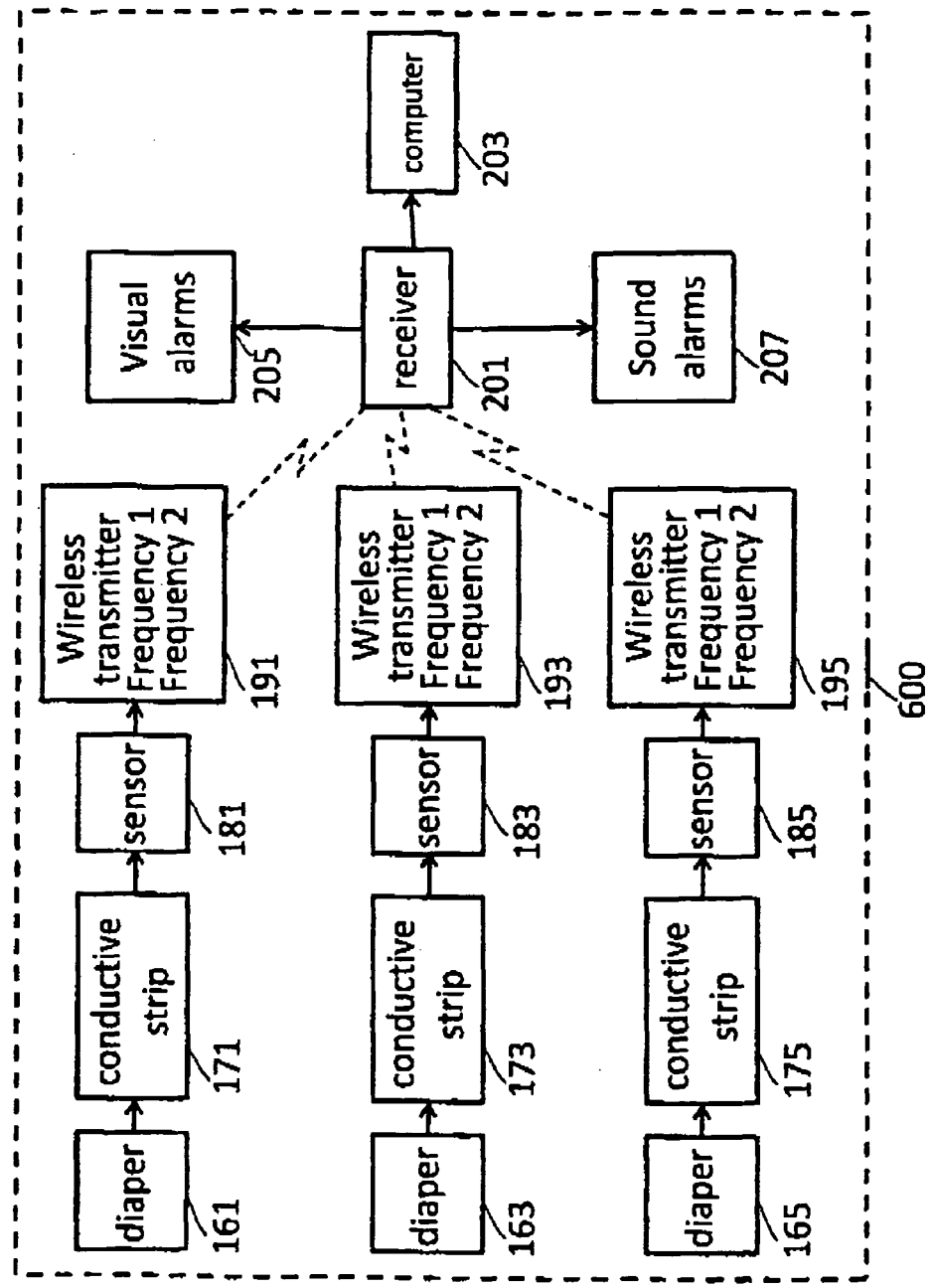
FIG. 6 illustrates a block diagram representing embodiments of the present invention disposable diaper with wireless alarm system involving multiple diapers each with different double frequency transmissions to set off a wet diaper alarm and to identify the wet diaper and to separately set off a disconnect alarm and to identify the disconnected diaper and further includes a computer controlled system.

FIG. 6 illustrates a block diagram representing embodiments of the present invention disposable diaper with wireless alarm system 600 involving multiple diapers each with different double frequency transmissions to set off a wet diaper alarm and to identify the wet diaper and to separately set off a disconnect alarm and to identify the disconnected diaper and further includes a computer controlled system. Different users wear diapers 161, 163 and 165 respectively, and each have conductive strips 171, 173 and 175, respectively. They have sensor/transmitters connected to each with wet diaper sensors and on/off sensors. Each transmitter has two different frequencies that are different from all of the other frequencies in the system. Specifically, sensors 181, 183 and 185 and wireless transmitters 191, 193 and 195 each have their own different wet diaper transmission frequency and their own different on/off transmission frequency. They cooperate to send timely wet diaper or disconnect transmissions to wireless receiver 201. When wireless receiver 201 receives a particular frequency signal, it will set off an identifying alarm and will preferably include both visual alarm 205 and sound alarm 207. Computer 203 functions in any manner similar to computer 155 described above in conjunction with FIG. 5.

Figure 7:
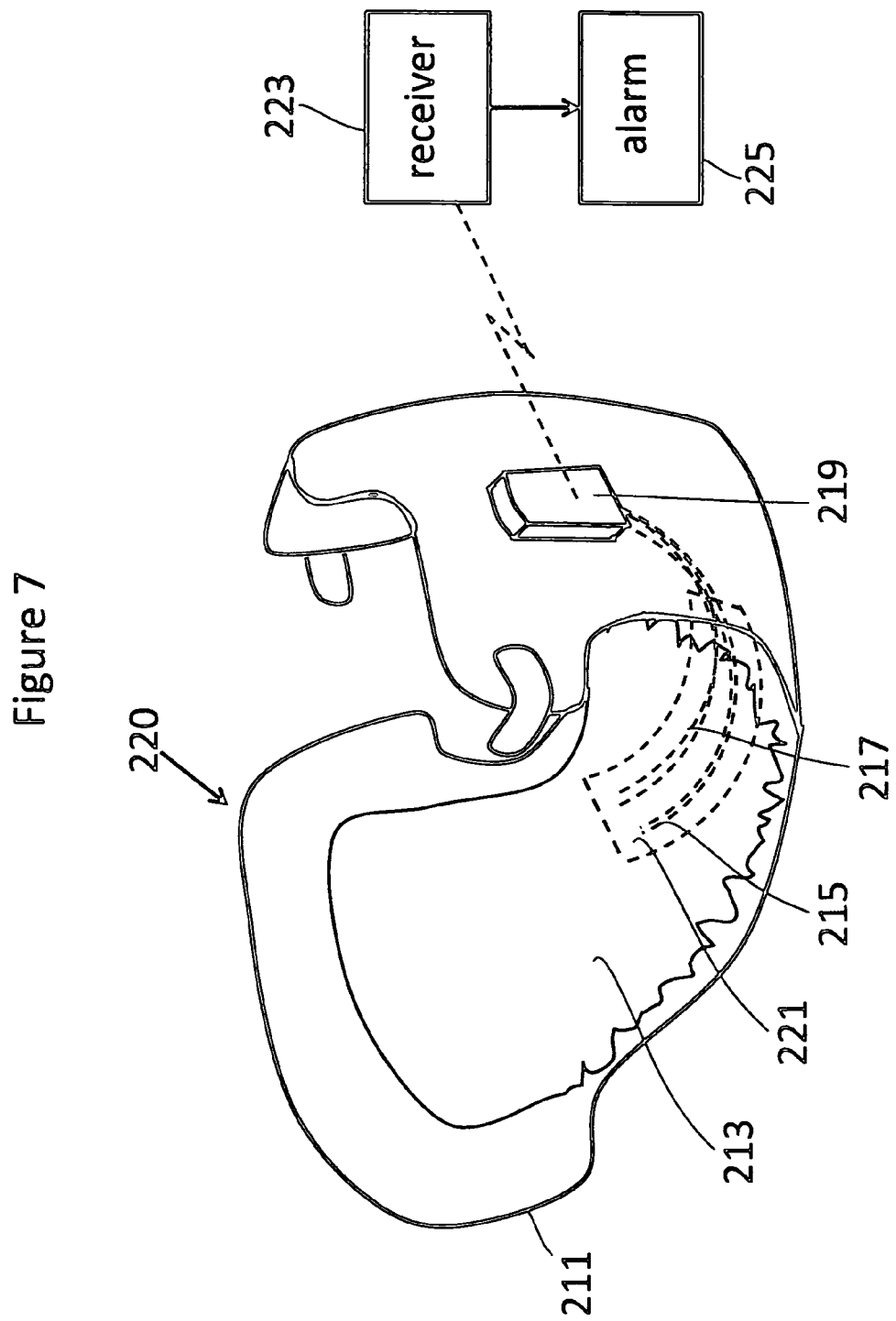
FIG. 7 shows a perspective view of a present invention diaper with diagrammatic representations of the receiver and alarm.

FIG. 7 shows a perspective view of a present invention diaper 220 with diagrammatic representations of the receiver 223 and alarm 225. Diaper 223 has a screen layer 213 that is an inside layer, a middle absorbent layer (not identified), and an outer layer 211, being a barrier layer. There is a conductive strip 221 with a first conductive band 215 and a second conductive band 217 that plug into sensor/transmitter 219. Between conductive bands 215 and 217 is a non-conductive band to keep the circuit non-functioning. However, when a liquid, such as urine, contacts both conductive bands in a continuum, the circuit is completed, the sensor 219 recognizes this, and transmits a "wet diaper" signal to receiver 223, that then sets off alarm 225.

Figure 8:
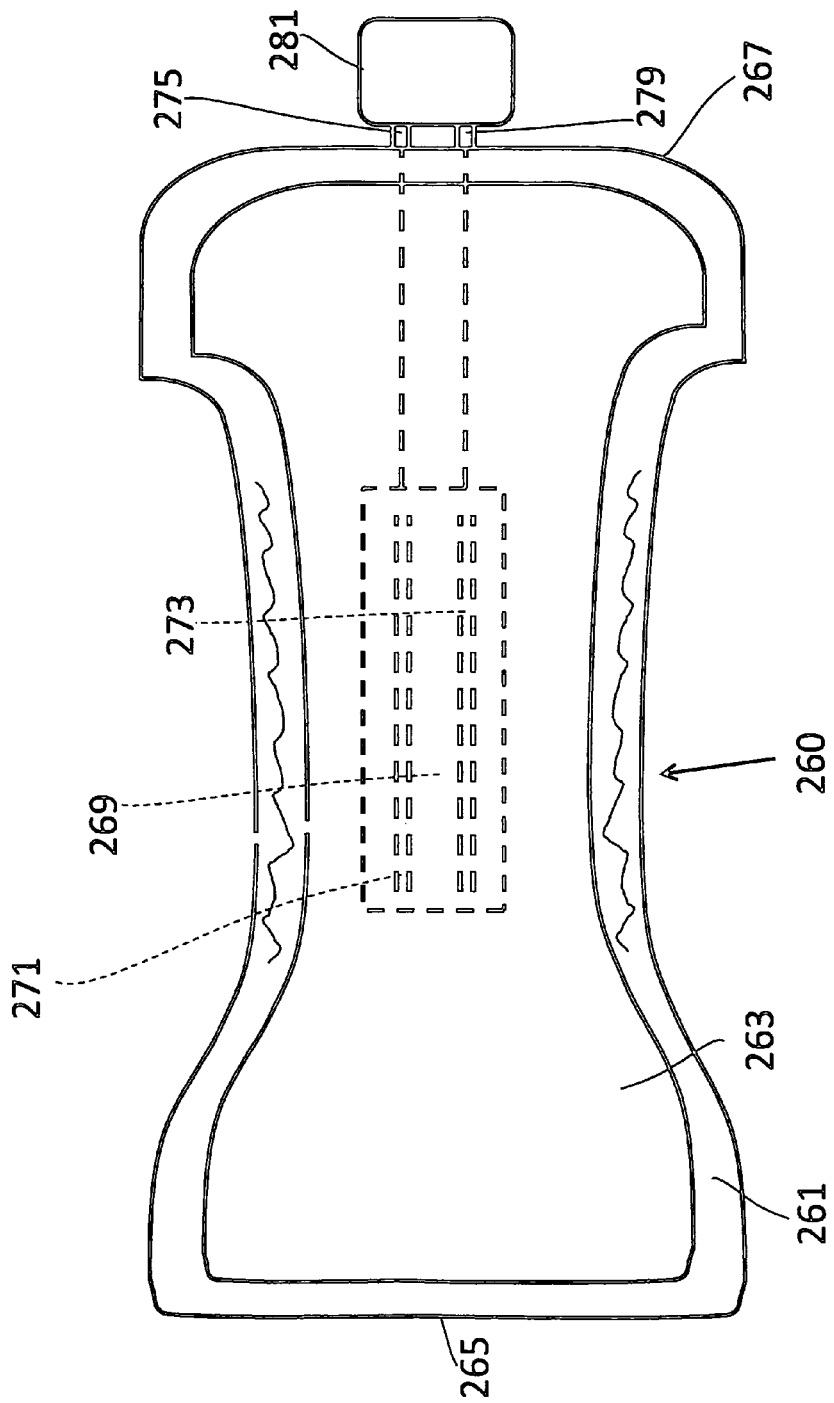
FIG. 8 shows a top view of a present invention diaper.

FIG. 8 shows a top view of a present invention diaper 260. Diaper 260 includes a screen layer 263, an absorbent middle layer 261 and a barrier layer 265. At the front 267 of diaper 260 are plug contacts 275 and 279 that are plugged into sensor/transmitter 281. As can be seen from this top view, the conductive, strip is located in the center diaper 260 so as to be in the bottom area when worn. When non-conductive band 269 is welted so that conductive strips 271 and 273 are in contact with the same "puddle" and alarm signal is transmitted by sensor/transmitter 281. The present invention system otherwise operates in a manner similar to that described in conjunction with FIG. 7 above.

FIGS. 9, 10, 11 and 12 show side partial views of present invention diapers with the conductive strips being positioned above the absorbent padding, within the absorbent padding, between the absorbent padding and the protective outer layer and within the protective outer layer, respectively. In all of these Figures, the inside, screen layer is not shown and all of the views are side, partial views. In FIG. 9, diaper 270 has conductive strip 275 located above barrier layer 273 and above absorbent padding 271. In FIG. 10, diaper 280 has conductive strip 285 located within absorbent padding 281 and above barrier layer 283. In FIG. 11, diaper 290 shows conductive strip 295 located between absorbent padding 281 and barrier layer 283. In FIG. 12, diaper 310 shows conductive strip 315 embedded in barrier layer 313 and below absorbent layer 311. It should now be clear that the conductive strip could be located in or between any of the layers of the diaper and traverse more than one layer, without exceeding the scope of the present invention.

Figure 13:
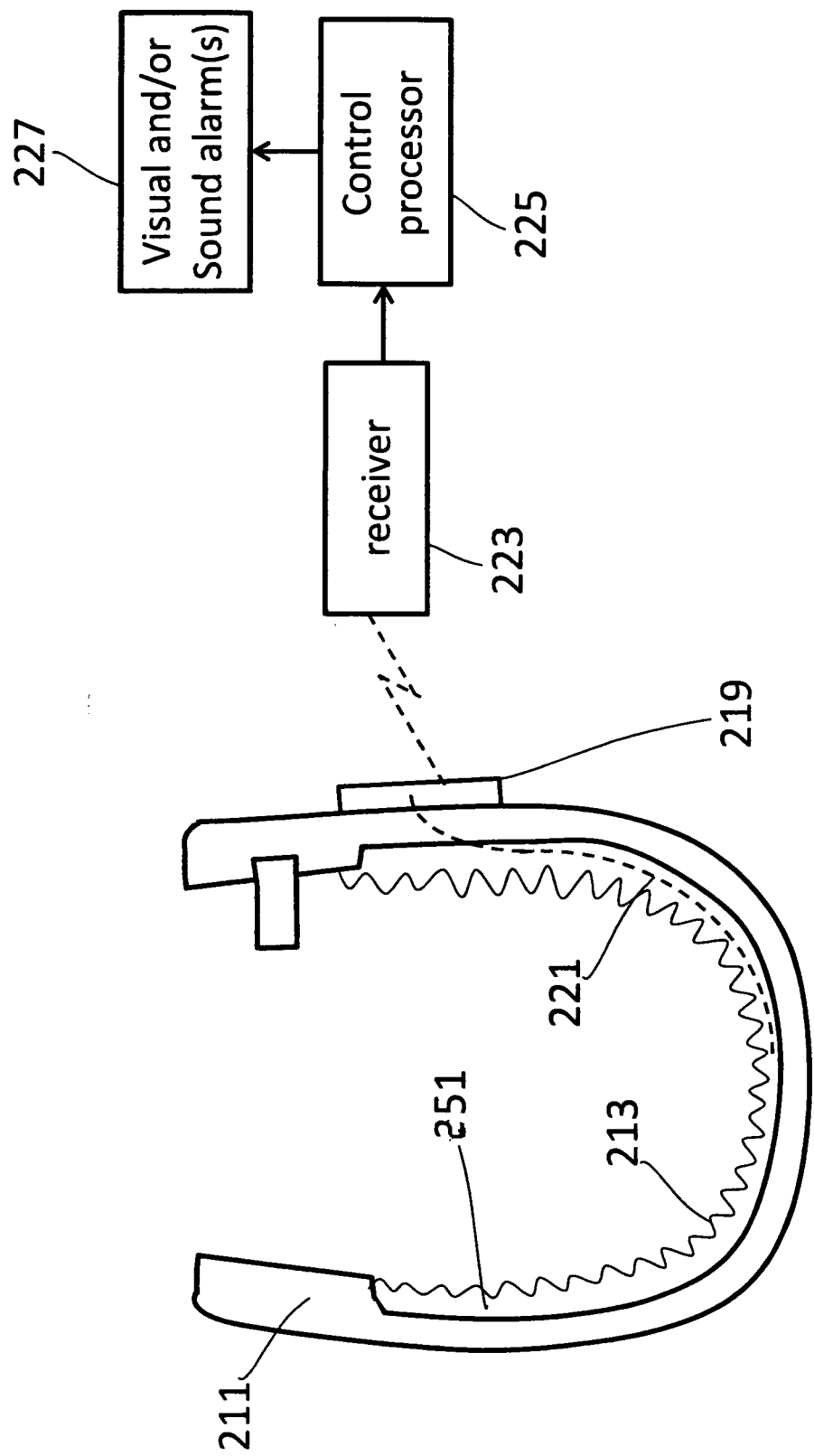
FIG. 13 shows a side view of another single diaper present invention system.

FIG. 13 shows a side view of another present invention single diaper system. The present invention diaper shown in FIG. 13 has an outer barrier layer 211, an inner screen layer and a middle absorbent layer 251. Conductive strip 221 is connected to sensor/transmitter 219. When a wet diaper problem or disconnected diaper problem is detected, the appropriate signal is sent to receiver 223, which is processed by control processor 225 to set off alarm(s) 227.

Figure 14:
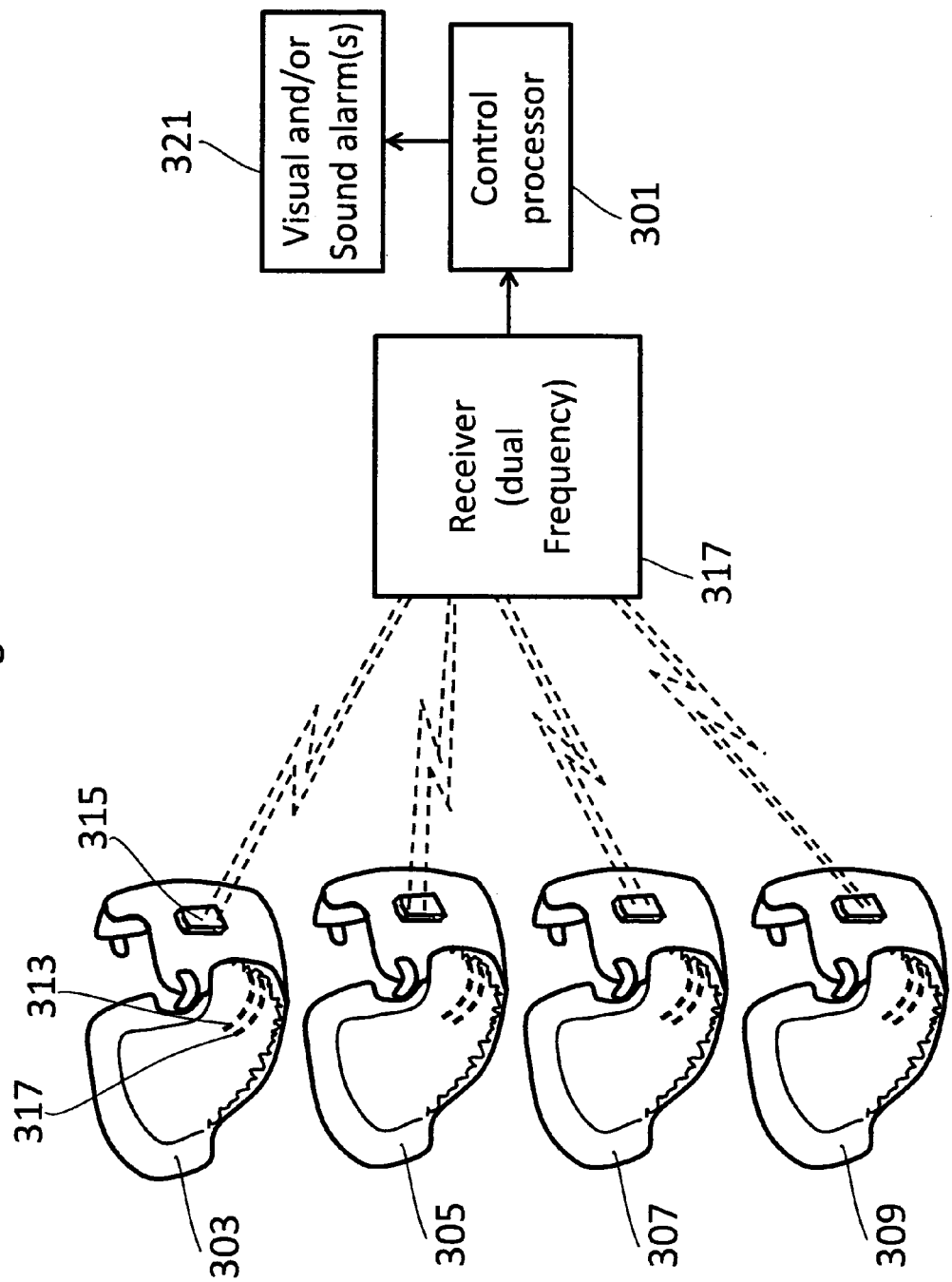
FIG. 14 shows a present invention system with a plurality of diapers.

FIG. 14 shows a present invention system with a plurality of diapers. Diaper 303 has separated conductive bands 313 and 317 connected to sensor/transmitter 315, and these operate similarly to the diapers described in other embodiments set forth above. Also, diapers 305, 307 and 309 have similar features except that each sensor/transmitter has two different frequencies, each also different from all other different frequencies. Receiver 317 receives warning signals with discrimination and identification via control processor 301, which in turn, send out appropriate alarm(s) 321.

They following describe the Figures that present various connection options for the present invention system diaper conductive strip/sensor connections.

Figure 15:
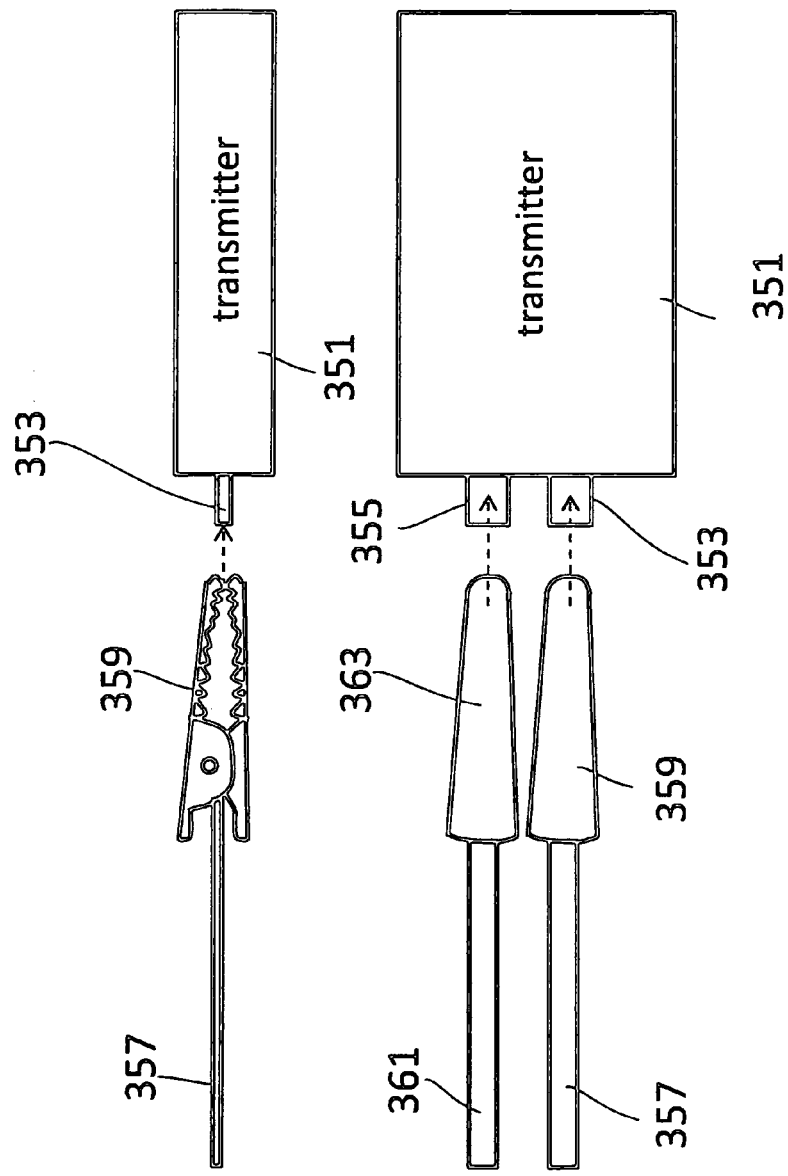
FIGS. 15A and 15B show side and top views of a present invention transmitter connection using clip connectors.

FIGS. 15A and 15B show side and top views of a present invention transmitter connection using clip connectors 359 and 363. They each have wires 357 and 361 connected to conductive bands (not shown). They clip onto contacts 353 and 355 of sensor/transmitter 351.

FIGS. 16A and 16B show side and top views of a present invention transmitter connection using plug connector 407. Plug connector 407 has band wires 405 and 411 and plug prongs 409 and 415 that plug into socket 403 of sensor/transmitter 401.

FIGS. 17A and 17B show side and top views of a present invention transmitter connection using snap-in plug connectors. Snap-in connector 457 includes band wires 455 and 465, and plug prongs 459 and 461 for receptacle receivers 463 and 467 of sensor/transmitter 451. Note that protrusion 473 snaps into recess 475 to secure the connection.

As demonstrated and suggested, many different connection arrangements may be utilized without exceeding the scope of the present invention.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims. For example, while it is preferable to reuse the sensor/transmitter devices of the present invention, it is not required to do so and the devices may thus be configured accordingly.

What is claimed is:

1. A disposable diaper with wireless alarm system, which comprises:
   (a) a disposable diaper structure having at least an inside layer, being a screen layer, a middle layer, being an absorbent layer, and an outer layer, being a barrier layer, and further having at least one fastening mechanism for affixing said disposable diaper structure to a person;
   (b) a disposable conductive strip located within said disposable diaper structure, and having two conductive bands and a non-conductive band between said two conductive bands, said two conductive bands being spaced sufficiently to have an open circuit when dry and to have a closed circuit when said strip is wet with urine;
   (c) an attachable, removable, reusable battery-powered sensor-transmitter device attached to said disposable diaper structure and electrically connected to said two conductive bands of said disposable conductive strip, said sensor-transmitter device having a predetermined frequency for transmittal to a wireless receiver;

(d) said wireless receiver having an alarm signal and being remotely located from said sensor-transmitter device, and set to receive a transmission therefrom;

wherein, when said disposable contact strip is dry, said sensor-transmitter device does not transmit an alarm signal to said wireless receiver, and when said disposable contact strip is wet with urine to close said circuit, said sensor-transmitter device sends an alarm signal to said wireless receiver, triggering activation of said alarm signal to advise a caretaker that said disposable diaper structure is wet.

2. The disposable diaper with wireless alarm system of claim 1 wherein said disposable conductive strip is permanently positioned within said disposable diaper structure.

3. The disposable diaper with wireless alarm system of claim 1 wherein said disposable conductive strip is located between said inside layer and said middle layer of said disposable diaper structure.

4. The disposable diaper with wireless alarm system of claim 1 wherein said disposable conductive strip is located within said middle layer of said disposable diaper structure.

5. The disposable diaper with wireless alarm system of claim 1 wherein said disposable conductive strip is located between said middle layer and said outer layer of said disposable diaper structure.

6. The disposable diaper with wireless alarm system of claim 1 wherein said disposable conductive strip is electrically connected to said sensor-transmitter device by a connector mechanism selected from the group consisting of a plug, a hook and loop mechanism, a slide-in receiver for said strip and external contacts.

7. A disposable diaper with wireless alarm system, which comprises:

(a) a disposable diaper structure having at least an inside layer, being a screen layer, a middle layer, being an absorbent layer, and an outer layer, being a barrier layer, and further having at least one fastening mechanism for affixing said disposable diaper structure to a person;

(b) a disposable conductive strip located within said disposable diaper structure, and having two conductive bands and a non-conductive band between said two conductive bands, said two conductive bands being spaced sufficiently to have an open circuit when dry and to have a closed circuit when said strip is wet with urine;

(c) an attachable, removable, reusable battery-powered sensor-transmitter device attached to said disposable diaper structure and electrically connected to said two conductive bands of said disposable conductive strip, said sensor-transmitter device having a first predetermined frequency for transmittal to a wireless receiver to indicate that said disposable conductive strip is electrically connected to said sensor-transmitter device and having a second predetermined frequency for transmittal to said wireless receiver when said disposable conductive strip circuit is closed, indicating a wet diaper;

(d) said wireless receiver, being remotely located from said sensor-transmitter device, and set to receive a transmissions therefrom, and having a first receiver corresponding to said first predetermined frequency and having a having a first predetermined frequency connect signal, to show that said disposable conductive strip is electrically connected to said sensor-transmitter device, and having a second receiver corresponding to said second predetermined frequency and alarm signal, for activation of a wet diaper structure alarm signal;

(e) wherein, when said disposable contact strip is dry, said sensor-transmitter device does not transmit an alarm signal to said wireless receiver, and when said disposable contact strip is wet with urine to close said circuit, said sensor-transmitter device sends an alarm signal to said wireless receiver, triggering activation of said alarm signal to advise a caretaker that said disposable diaper structure is wet.

8. The disposable diaper with wireless alarm system of claim 7 wherein said disposable conductive strip is permanently positioned within said disposable diaper structure.

9. The disposable diaper with wireless alarm system of claim 7 wherein said disposable conductive strip is located between said inside layer and said middle layer of said disposable diaper structure.

10. The disposable diaper with wireless alarm system of claim 7 wherein said disposable conductive strip is located within said middle layer of said disposable diaper structure.

11. The disposable diaper with wireless alarm system of claim 7 wherein said disposable conductive strip is located between said middle layer and said outer layer of said disposable diaper structure.

12. The disposable diaper with wireless alarm system of claim 7 wherein said disposable conductive strip is electrically connected to said sensor-transmitter device by a connector mechanism selected from the group consisting of a plug, a hook and loop mechanism, a slide-in receiver for said strip and external contacts.

13. A disposable diaper wireless alarm system for a plurality of diapers being worn by a plurality of different users, which comprises:

A) a plurality of disposable diapers, each one to be worn by a plurality of different users, each of said disposable diapers including:

(a) a disposable diaper structure having at least an inside layer, being a screen layer, a middle layer, being an absorbent layer, and an outer layer, being a barrier layer, and further having at least one fastening mechanism for affixing said disposable diaper structure to a person;

(b) a disposable conductive strip located within said disposable diaper structure, and having two conductive bands and a non-conductive band between said two conductive bands, said two conductive bands being spaced sufficiently to have an open circuit when dry and to have a closed circuit when said strip is wet with urine;

(c) an attachable, removable, reusable battery-powered sensor-transmitter device attached to said disposable diaper structure and electrically connected to said two conductive bands of said disposable conductive strip, said sensor-transmitter device having a predetermined frequency for transmittal to a wireless receiver, and wherein each attachable, removable, reusable battery-powered sensor-transmitter device of said plurality of disposable diapers having different frequencies from all other attachable, removable, reusable battery-powered sensor-transmitter devices so as to identify each user by signals corresponding to said frequencies;

B) said wireless receiver, being remotely located from said sensor-transmitter devices, and set to receive transmissions therefrom, and having plurality of receiver corresponding to said different predetermined frequencies of said sensor-transmitter devices for activation of a wet diaper structure alarm signals; and, C) a controller processor connected to said wireless receiver having software to recognize, distinguish and identify different frequency signals and correlate them to specific transmitters by at least one parameter selected from the group consisting of a unique character identifier, a patient identifier, a transmitter identifier and a location identifier;

wherein, when said disposable contact strip is dry, said sensor-transmitter device does not transmit an alarm signal to said wireless receiver, and when said disposable contact strip is wet with urine to close said circuit, said sensor-transmitter device sends an alarm signal to said wireless receiver, triggering activation of said alarm signal to advise a caretaker that said disposable diaper structure is wet.

14. The disposable diaper wireless alarm system of claim 13 wherein said disposable conductive strip is permanently positioned within said disposable diaper structure.

15. The disposable diaper wireless alarm system of claim 13 wherein said disposable conductive strip is located between said inside layer and said middle layer of said disposable diaper structure.

16. The disposable diaper wireless alarm system of claim 13 wherein said disposable conductive strip is located within said middle layer of said disposable diaper structure.

17. The disposable diaper wireless alarm system of claim 13 wherein said disposable conductive strip is located between said middle layer and said outer layer of said disposable diaper structure.

18. The disposable diaper wireless alarm system of claim 13 wherein said disposable conductive strip is electrically connected to said sensor-transmitter device by a connector mechanism selected from the group consisting of a plug, a hook and loop mechanism, a slide-in receiver for said strip and external contacts.

19. The disposable diaper wireless alarm system of claim 13 wherein each of said sensor-transmitter devices has a first predetermined frequency for transmittal to said wireless receiver to indicate that said disposable conductive strip is electrically connected to said sensor-transmitter device, and has a second predetermined frequency for transmittal to said wireless receiver when said disposable conductive strip circuit is closed, and wherein each attachable, removable, reusable battery-powered sensor-transmitter device frequency of said plurality of disposable diapers are different frequencies from all other attachable, removable, reusable battery-powered sensor-transmitter device frequencies so as to identify each user by signals corresponding to said frequencies.

20. The disposable diaper wireless alarm system of claim 19 wherein said system controller processor further includes software, storage and display means to create individual histories of individual diaper structure conductive strip connections, wet alarms and restoration to new diapers, said histories being arranged by at least one parameter selected from the group consisting of a unique character identifier, a patient identifier, a transmitter identifier and a location identifier.

* * * * *